United States Patent
Ragsdale (10) Patent No.: US 7,923,238 B2
(45) Date of Patent: Apr. 12, 2011

(54) MULTI-CHANNEL ELECTROPORATION SYSTEM

(75) Inventor: Charles W. Ragsdale, Concord, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 320 days.

(21) Appl. No.: 11/567,373

(22) Filed: Dec. 6, 2006

(65) Prior Publication Data

US 2007/0231873 A1    Oct. 4, 2007

Related U.S. Application Data (60) Provisional application No. 60/826,422, filed on Sep. 21, 2006, provisional application No. 60/771,994, filed on Feb. 10, 2006.

(51) Int. Cl.
   *C12M 1/42* (2006.01)
   *C12M 3/00* (2006.01)
   *C12N 13/00* (2006.01)

(52) U.S. Cl. .......... 435/285.2; 435/288.4; 435/173.1; 435/173.4; 435/173.5; 435/173.8; 435/287.2; 435/288.2; 435/288.3; 435/173.6; 204/403.01

(58) Field of Classification Search .......... 435/285.2, 435/288.4, 173.1, 173.4, 173.5, 173.8, 287.2, 435/288.2, 288.3, 173.6; 204/403.01
See application file for complete search history.

(56) References Cited

U.S. PATENT DOCUMENTS

| | | | |
|---|---|---|---|
| 4,471,276 A | 9/1984 | Cudlitz | |
| 4,484,122 A | 11/1984 | Day et al. | |
| 4,520,296 A | 5/1985 | Lepper et al. | |
| 4,540,944 A | 9/1985 | Watanabe | |
| 5,027,083 A | 6/1991 | Kutzavitch et al. | |
| 5,170,429 A | 12/1992 | Stocklin et al. | |
| 5,269,937 A | 12/1993 | Dollinger et al. | |
| 5,363,070 A | 11/1994 | Arimoto | |
| 5,642,035 A | 6/1997 | Ragsdale | |
| 5,656,926 A | 8/1997 | Ragsdale | |
| 5,729,426 A | 3/1998 | Ragsdale | |
| 5,891,179 A | 4/1999 | Er et al. | |
| 6,258,592 B1 * | 7/2001 | Ragsdale et al. | 435/285.2 |
| 6,356,086 B1 | 3/2002 | Cook et al. | |
| 6,686,193 B2 * | 2/2004 | Maher et al. | 435/285.2 |
| 6,771,082 B2 | 8/2004 | Ragsdale et al. | |
| 6,798,175 B2 | 9/2004 | Hanada et al. | |
| 6,856,119 B2 | 2/2005 | Crawford | |
| 7,054,685 B2 | 5/2006 | Dimmer et al. | |

(Continued)

FOREIGN PATENT DOCUMENTS

WO    WO 2004/050866 A1    6/2004

OTHER PUBLICATIONS

U.S. Appl. No. 11/567,438, filed Dec. 6, 2006.

(Continued)

*Primary Examiner* — Nathan A Bowers (74) *Attorney, Agent, or Firm* — David B. Raczkowski; Kilpatrick Townsend & Stockton LLP (57) ABSTRACT

Systems, methods and apparatus provide flexible and efficient high throughput electroporation systems. An electrical pulse may be transmitted to any number of channels of a multi-channel sample plate. Drivers can provide the selection of which channels to transmit the electrical pulse. To provide efficient transitions between electrical pulses, discharge circuits provide efficient means achieve a desired voltage.

25 Claims, 7 Drawing Sheets

U.S. PATENT DOCUMENTS

| | | |
|---|---|---|
| 2002/0090649 A1* | 7/2002 | Chan et al. ............... 435/7.1 |
| 2003/0026092 A1 | 2/2003 | Reese et al. |
| 2003/0214269 A1 | 11/2003 | Shiue |
| 2004/0171962 A1 | 9/2004 | Leveque et al. |
| 2005/0054969 A1* | 3/2005 | Hoff et al. ............... 604/20 |
| 2005/0112544 A1* | 5/2005 | Xu et al. ............... 435/4 |
| 2005/0213374 A1* | 9/2005 | Xu et al. ............... 365/156 |
| 2006/0087522 A1* | 4/2006 | Muller-Hartmann et al. .... 347/1 |
| 2006/0115888 A1 | 6/2006 | Gamelin et al. |
| 2007/0194759 A1 | 8/2007 | Shimizu et al. |
| 2008/0024079 A1 | 1/2008 | Matsubara et al. |

OTHER PUBLICATIONS

U.S. Appl. No. 60/826,422, filed Sep. 21, 2006.
U.S. Appl. No. 11/857,679, filed Sep. 19, 2007.

* cited by examiner

MULTI-CHANNEL ELECTROPORATION SYSTEM

CROSS-REFERENCES TO RELATED APPLICATIONS

The present application is related to the following commonly-assigned concurrently filed U.S. patent application No. 11/567,438 now U.S. Pat. No. 7,567,549, entitled "MEASURING SAMPLE RESISTANCE IN ELECTROPORATION," by Ragsdale (hereinafter Ragsdale II), which is incorporated herein by reference for all purposes.

The present application is also related to the following commonly-assigned U.S. Provisional Patent Applications: No. 60/771,994, entitled "APPARATUS FOR HIGH-THROUGHPUT ELECTROPORATION," by Ragsdale et al., filed Feb. 10, 2006, and U.S. Provisional Patent Application No. 60/826,422 entitled RESISTOR PULSE MODULATION, by Ragsdale, filed Sep. 12, 2006, which are herein incorporated by reference in their entirety.

BACKGROUND OF THE INVENTION

The present invention relates generally to electroporation systems, and more particularly to providing flexible and efficient high throughput electroporation systems.

Electroporation is a technique that involves the use of an electric field to impregnate living biological cells, liposomes, and vesicles with exogenous molecules. High-throughput electroporation allows a user to apply an electric field, i.e., to "shock," multiple samples either simultaneously or automatically in sequence. With the heightened interest in siRNA experiments, research using cDNA libraries, and the desire to perform rapid electroporation optimization, high-throughput electroporation is needed and demanded by scientists.

Electroporation occurs within a narrow range of parameters, such as pulse voltage and pulse duration, which is exhibited by a narrow window between electrocution and little or no electroporation. For example, if a pulse with too long a duration or too high a field strength is used, the cells may be lysed (destroyed). If the duration or field strength of a pulse is too low, electroporation efficiency is lost. The efficiency of electroporation is dependent on the cells, biological parameters, voltage, time constant (or duration), waveshape, current, heating, arcs, and other parameters. These parameters may adversely effect certain high-throughput electroporation systems.

One manufacturer (BTX Instrument Division, Harvard Apparatus, Inc., Holliston, Mass., USA) offers a high-throughput electroporator, which is described in U.S. Patent Publication 2006/0115888 (and PCT Publication No. WO 2004/050866 A1), the contents of which are incorporated herein by reference. The plates described in the above-cited patent applications have rectangular wells that contain plated electrodes. There are 96 wells arranged into 12 columns with 8 wells per column.

All of the electrodes on one side of a bank (i.e., a column) of eight wells are connected in common to plated traces along each bank, and all electrodes of the other side of the wells in the same bank are likewise connected in common. The plated traces end in electrical contacts, resulting in one anode contact and one cathode contact for each column. The electroporation plate is lowered into a device called a plate handler to place the plate into position for use. The plate handler connects with the 24 electrical contacts of the 12 banks of wells and has switches that connect each of the 12 banks in sequence to an external electroporator. Electric pulses are then delivered in sequence.

Since most cells live best in normal saline, shocking is typically performed in cells suspended in normal saline or other high-conductivity buffers. Wells containing normal saline present a relatively low resistance, which limits the electric current provided by the above electroporator since it is configured to shock eight wells at once. For example, it also causes a low resistance load (about 6.25 ohms) for the electroporator. Because of the low resistance of eight parallel wells and the fact that the maximum capacitor available has a capacitance of about 3200 mfd, the maximum time constant is limited to about 20 msec.

Thus, the electroporator is limited to shocking all 8 wells of a bank (column) simultaneously, and each bank is shocked separately. As explained above, this rigid operation limits the pulse width for many samples. Additionally, it prevents even more rapid electroporation by limiting the number of samples to eight. Also if all 12 banks are shocked, it takes about ten minutes of time for many protocols.

Therefore, it is desirable to provide electroporation system having flexibility in providing electrical pulses to many numbers of samples, and is also desirable to provide a sequence of pulses more efficiently.

BRIEF SUMMARY OF THE INVENTION

The present invention provides systems and methods of providing flexible and efficient high throughput electroporation systems. These systems and methods employ one or more techniques such as connecting any number of banks (channels) of a sample plate together for receiving the same electrical pulse (e.g. using return drivers) and providing more efficient transitions between delivering two electrical pulses using specialized discharge circuits.

According to an exemplary embodiment, an electroporation system has a capacitance and a charging circuit configured to charge the capacitance. A first electrical connector of the system is adapted to connect with a common pad of a sample plate, which has multiple banks. Each bank has multiple wells. When the first electrical connector is connected with the common pad, the first electrical connector is connected with a first electrode of each well of the banks. The first electrical connector may be connected to a high voltage side of the sample plate or the low voltage side of the sample plate.

Drivers are each adapted to connect with a bank-specific pad of the sample plate. When a driver is connected with a banks-specific pad, that driver is connected with a second electrode of each well of the specific bank. A state of that driver determines whether an electrical pulse is transmitted from the capacitance to the specific bank connected with that driver. Any number of drivers may be in a state to transmit the electrical pulse to any number of banks, including all of the banks. In one embodiment, the drivers are connected with the capacitance, i.e. in the circuit on one side of the sample plate. In another embodiment, the drivers are connected with a common return path, i.e. in the circuit on another side of the sample plate.

In one embodiment, a memory element is configured to store parameters for each electrical pulse to be delivered to the banks. The parameters may include which banks to deliver each electrical pulse. In another embodiment, a control processor independently controls the state of each of the drivers. In another embodiment, a control processor is configured to determine a resistance of the banks and control the state of each driver based on the resistance.

According to another exemplary embodiment, a resistance of at least one bank is measured. This resistance is used to select one or more banks in which to deliver an electrical pulse. One or more parameters for the electrical pulse may also be used to select the banks. An electrical pulse is then transmitted to the selected banks. In one embodiment, the resistance is measured by determining whether the resistance is within two or more ranges of resistance values. The resistance of each selected bank may be measured, and the resistance of every bank may be measured.

In one embodiment, the resistance of the selected banks is determined. Based on this resistance, the resistance of a variable resistance device that is connected in parallel with the selected banks may be determined. In another embodiment, a driver that is coupled to each selected bank is turned "on" so as to transmit the electrical pulse to that bank.

According to another exemplary embodiment, an electroporation system has a set of capacitors, a control processor configured to select one or more of the capacitors to achieve a desired capacitance, and a charging circuit configured to charge the selected capacitors. To decrease a charge on the selected capacitors in an efficient manner, discharge circuits are selectively connected with the selected capacitors. Each discharge circuit may be designated to be connected with a different range of capacitances. In one embodiment, a discharge circuit includes a pulse modulated resistor. In another embodiment, a discharge circuit includes a switching device, which may be a silicon controlled rectifier.

In one embodiment, a memory element stores the capacitances of each capacitor in the set of capacitors. In another embodiment, based on the desired capacitance, the control processor is configured to select one of the discharging circuits to decrease the charge on the selected capacitors until a desired voltage is obtained. In another embodiment, the charging circuit is configured to charge the selected capacitors to a voltage greater than a desired voltage.

According to another exemplary embodiment, one or more capacitors are selected to achieve a desired capacitance. The selected capacitors are charged to a higher voltage than the desired voltage. Based on the desired capacitance, one of a plurality of discharge circuits are selected to connect with the selected capacitors. The selecting of a discharge circuit may also be based on other quantities, such as a desired voltage. The selected discharge circuit removes charge from the selected capacitors until the desired voltage is reached. The resistance of the selected discharge circuit may be controlled with a pulse modulated signal.

In one embodiment, an electrical pulse is transmitted from the selected capacitors to a sample load. In one aspect, subsequent to transmitting the electrical pulse, a second of the discharge circuits is selected, based on the desired capacitance, to connect with at least a portion of the selected capacitors. The second selected discharge circuit is then used to remove charge from the portion of the selected capacitors until a second desired voltage is reached.

In another embodiment, prior to selecting the one discharge circuit, an electrical pulse is transmitted from the selected capacitors to a sample load. In one aspect, the desired voltage is a voltage just below a voltage for a next electrical pulse. In one embodiment, another one or more capacitors are selected to achieve another desired capacitance. The another selected capacitors are charged to a higher voltage than another desired voltage. Based on the another desired capacitance, a second of the discharge circuits is selected to connect to the selected another capacitors, and charge is removed from the selected another capacitors with the second selected discharge circuit until the voltage for the next electrical pulse is achieved.

Reference to the remaining portions of the specification, including the drawings claims and Appendices, will realize other features and advantages of the present invention. Further features and advantages of the present invention, as well as the structure and operation of various embodiments of the present invention, are described in detail below with respect to the accompanying drawings.

DETAILED DESCRIPTION OF THE INVENTION

Embodiments in accordance with the present invention provide systems and methods of providing flexible and efficient high throughput electroporation systems. In certain aspects, these systems and methods provide the ability to deliver a pulse to any number of banks (channels) of a sample plate and provide more efficient transitions between delivering two electrical pulses.

Figure 1:
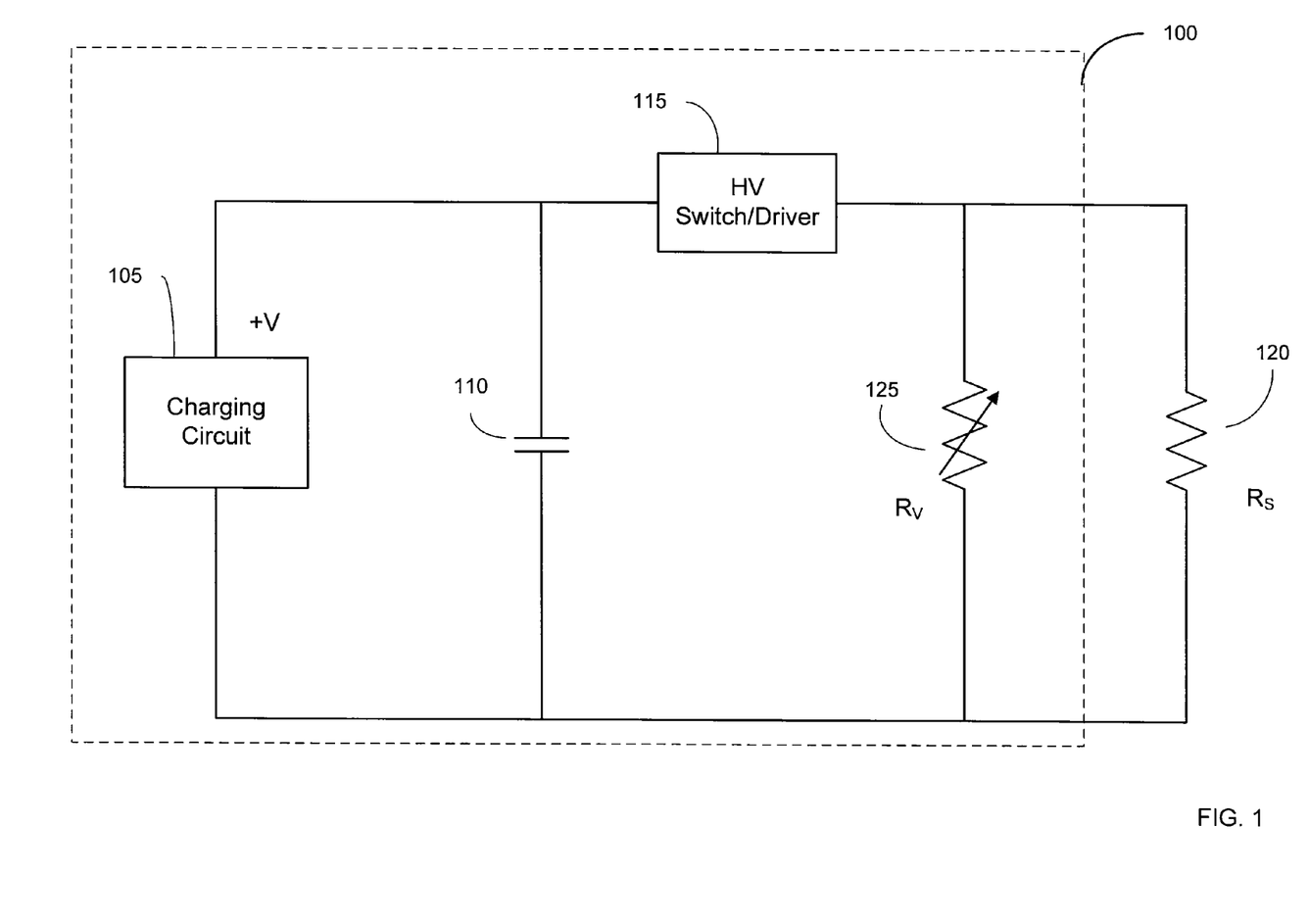
FIG. 1 illustrates an electroporation system according to an embodiment of the present invention.

FIG. 1 illustrates an electroporation system 100 according to an embodiment of the present invention. System 100 produces an electrical signal for sample load 120. A charging circuit 105 is connected with a capacitor 110 so as to charge capacitor 110 when switch 115, e.g. a high voltage (HV) switch, is open. In one aspect, charging circuit 105 is a power supply or some other constant-power or constant-current source. Capacitor 110 can also be set to different values. HV switch 115 connects capacitor 110 to sample load $R_S$ 120 and a variable resistor $R_V$ 125, which is connected in parallel with $R_S$ 120.

Once charging circuit 105 charges the capacitor 110 to a desired voltage HV switch 115 is closed. HV switch 115 may also be a driver with programmable parameters, such as number of pulses, pulse duration, and bursts of pulses. At this point, an electrical signal is transmitted to $R_S$ 120 and to $R_V$ 125. In one aspect the electrical signal is an exponentially decaying pulse, a truncated exponentially decaying pulse, or a square wave signal with droop.

The value of the resistance of $R_V$ 125 may be tuned to control the electrical signal. For example, for an exponentially decaying pulse, the resistance of $R_V$ 125 may be automatically determined such that a desired time constant $\tau = CR$ is substantially equal to the desired pulse duration, wherein $R = (R_S \times R_V)/(R_S + R_V)$ and C is the capacitance of capacitor 110.

The time constant may be chosen specifically based on the cells or other type of biomolecules in the sample load. As some cells may be sensitive or hard to transvect, a precisely controlled time constant can promote successful electroporation. Different resistances for $R_V$ 125 may be achieved as described in U.S. Provisional Patent Application No. 60/826, 422.

In instances, such as where multiple samples are to be tested or the parameters are to be optimized, sample load $R_S$ 120 may include multiple biological samples, each of which is to receive an electrical pulse. In such embodiments, the different samples may reside on a sample plate, such as a microtiter plate, which is arranged in a 2:3 rectangular matrix.

Figure 2:
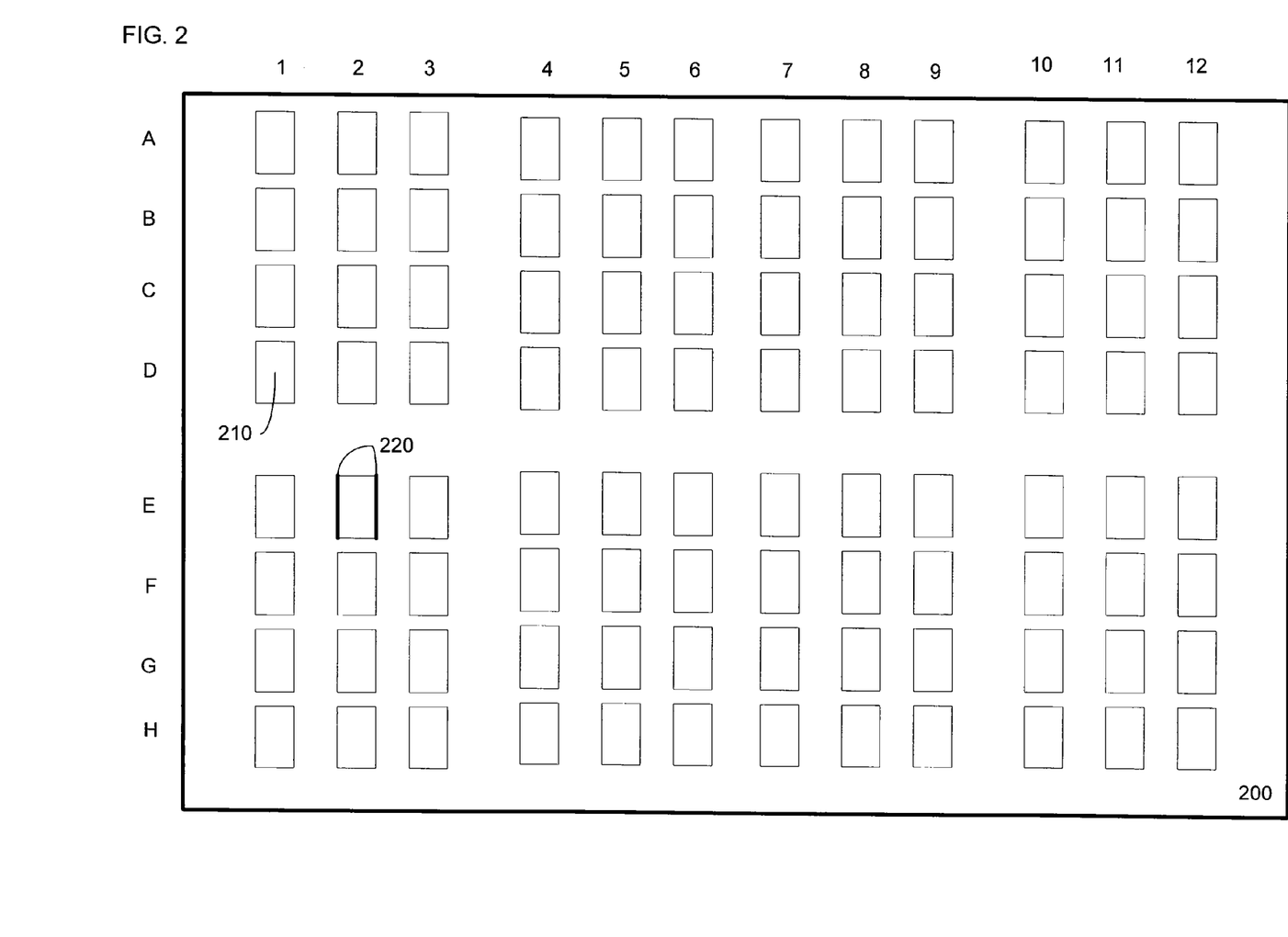
FIG. 2 illustrates a sample plate for use with embodiments of the present invention.

FIG. 2 illustrates a sample plate 200 for use with embodiments of the present invention. Other example sample plates may be found in application 60/771,994 referenced above. Sample biological molecules reside in the wells 210 to receive an electroporation pulse. Sample plates are preferably grouped into families, where the members of a plate family may differ in size. Each well 210 has electrodes, e.g., on opposing walls, for providing an electrical pulse to the sample biological molecules residing in the wells. A typical plate family allows electroporation in 96-well (12 columns of 8 wells each), 24-well, and 12-well formats, and other sizes as well, and allows the efficient use of adherent and non-adherent cells. (Adherent cells grow on surfaces; non-adherent cells can thrive either while floating or in solution).

These electroporation plates are useful with cell suspensions in phosphate-buffered saline (PBS) and are preferably designed to accommodate all standard 500V (mammalian) protocols, including standard protocols that require time constants (total resistance×capacitance) of at least 30 msec. In one embodiment, electroporation systems that use such plates allow up to 24 protocols on a single plate, where the protocols may differ in the following parameters: (a) waveform (exponential or square wave); (b) voltage 10-500V; (c) capacitance (25-3275-mfd); and (d) parallel resistance (50-1500 ohms).

The wells may be organized into 12 columns (1-12) and 8 rows (A-H), where the upper left most well is designated A1. In one embodiment having four wells per bank, the first four wells of a column (wells A-D) are part of one bank, and the next four wells (E-H) belong to another bank. Each well of bank would receive the same electrical pulse based on the same parameters. Thus, 24 different protocols may be implemented for a single plate. Twenty-four protocols also means twice the resistance for each bank presented to the electroporator, compared to the BTX system, which reduces the load on the electronics to a practical level In one aspect of the present invention, electrical connections provide the ability to select which wells to deliver an electrical pulse. These electrical connections may be on the plate, on a lid connected to the plate, or any other suitable location. In one embodiment, there is a common input pad and multiple output pads for the electrical pulse. In another embodiment, each electrode terminates in a pad 220 on the top surface of the electroporation plate such that contact can be made by a feature in the lid.

Figure 3:
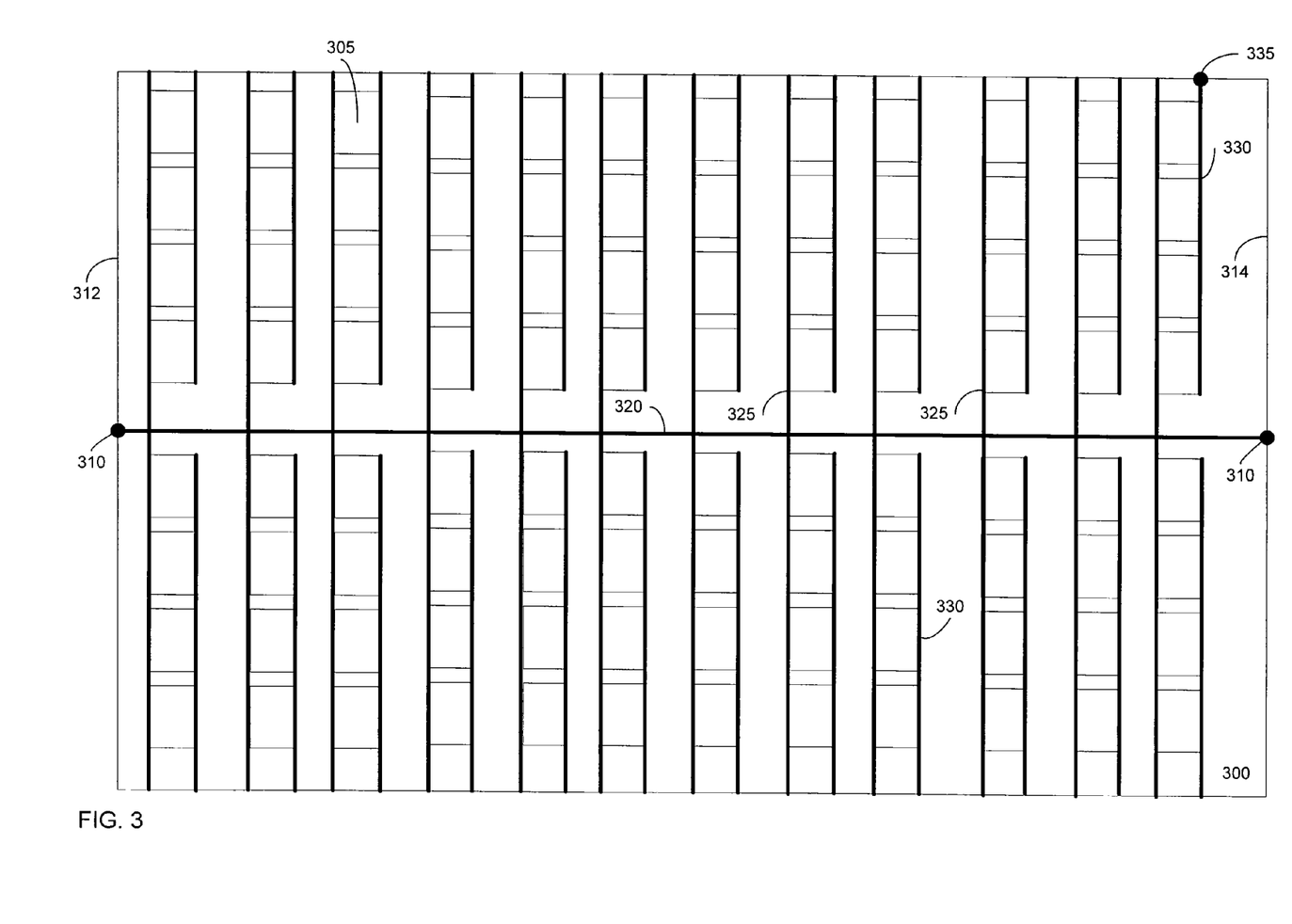
FIG. 3 illustrates a connecting lid for use with embodiments of the present invention.

FIG. 3 illustrates a connecting lid 300 for use with embodiments of the present invention. Other example sample plates may be found in application 60/771,994 referenced above. Rectangular boxes 305 illustrate the positioning of the wells 210. In one embodiment, each box 305 is a physical box that is sized such that the outside flats of the boxes mate with the top surface of the wells 210.

Connecting lid 300 has at least one common pad 310 at either one or both of the end edges 312, 314 of lid 300. A center wire 320 connects common pads 310 to common column wires 325, which, e.g., connect to pads 220 on sample plate 200. Common pad 310 may be adapted to receive any type of plug or connection to an outside power source, such as charging circuit 105, or to a lower potential, such as ground. In one embodiment, common pads 310 connect to one electrode of all of the wells. This connection may be along the same side of each column of wells, as depicted, or along alternating sides of the well, or any other suitable variation. Wire 320 and other wires may be vanes, traces, or any suitable medium for carrying an electrical pulse.

The other electrode of each well is connected to the opposite polarity of the common pad. For example, separate column wires 330 connect the opposite electrode of four wells (one bank) to a bank pad 335, which may be connected to a polarity opposite of common pad 310. In one embodiment, each separate column wire 330 connects to a pad having opposite polarity than common pad 310. Thus, the electrode polarity can be +− or −+ depending on the configuration of common column wires 325 and separate column wires 330. Alternating vanes make it easy to separate the + and− electrode plating when the plate is being manufactured, and may prevent arcing between adjacent columns. In one embodiment, separate column wires 330 may be used for the connection to the common pads; however, this would increase the number of common pads and additional spacing problems that follow. In another embodiment, electrodes are brought through each plate column end, e.g. at the plate bottom, to make contact with contacts in a chamber which holds the plate.

Accordingly, all wiring and electrical connections for the electrodes can be provided in connecting lid 300. This allows flexibility to connect the electrodes in any format by merely changing the lid. Once the appropriate connecting lid is placed on the electroporation plate, the assembly is slid into a slot of an electronic box, referred to as the high-throughput box. Contacts in the box make electrical connection with common pads 310 and bank pads 335 on the edges of connecting lid 300.

To provide an electrical pulse to a variable number of banks, a specified number of bank pads 335 are coupled together, e.g., to ground, for that electrical pulse. In one embodiment, this coupling is accomplished with a return driver. The driver may be formed by any semiconductor such as an IGBT, power FET, or bipolar transistor. SCR's might also be used. In one aspect, an "on" state of a driver incorporates a bank into the circuit so that it receives an electrical pulse, e.g. by connecting it to a charged capacitor. There may be a return driver for each channel, and the return driver may be a solid state device, such as an IGBT. CP 430 can independently control each driver such that any combination of the drivers may be "off" or "on".

In one embodiment, 4 to 96 wells in increments of four may be chosen to simultaneously deliver an electrical pulse, as depicted in FIG. 3. This flexibility in choosing the number of wells in which to deliver an electrical pulse allows for faster operation in some instances. For example, where the resistance of a well is quite large, an electrical pulse can be delivered to all of the wells at once. In aspect, to ensure that all banks are shocked with the same voltage as would be a single bank, resistor 125 and C 110 of FIG. 1 may require a change in resistance and capacitance, respectively. An increased voltage on C 110 to compensate for voltage drops in HV switch 115 and in wiring/contacts may also be done.

In other instances, this flexibility allows for greater variation in operating parameters. For example, when using cells in a saline environment, a well with about 4 mm spacing between the electrodes can have a low resistance of about 60 Ω, if the well is half full. Thus, having too many wells in parallel would create a sample load with a very low resistance, e.g., 60/96 Ω. When applying 500 V, the resulting current would be about 700 amps, which would be outside the range of standard components and would cause regulatory concerns. Applying a 500V pulse to only four wells (~15 Ω) would give only 35 amps.

Figure 4:
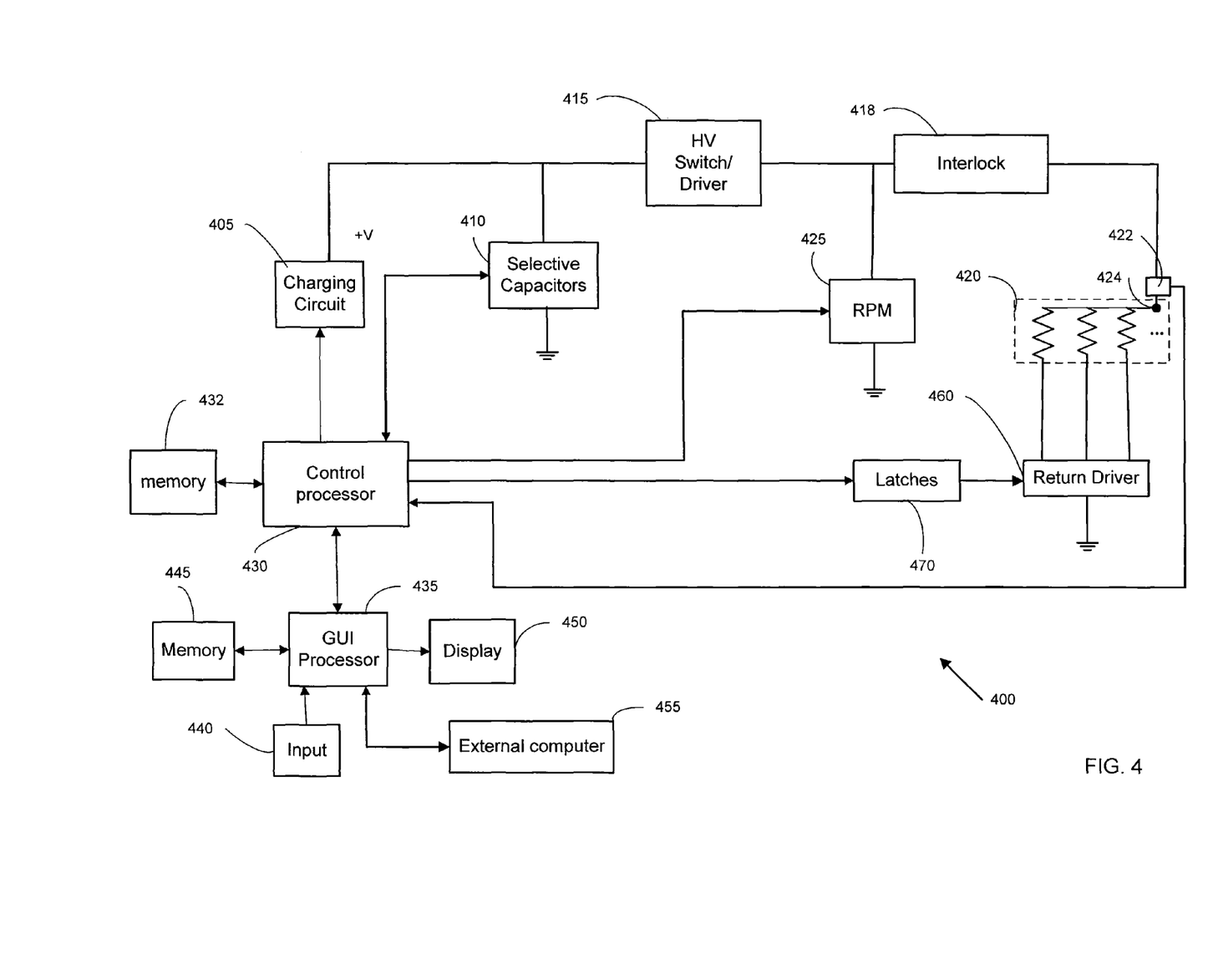
FIG. 4 illustrates an electroporation system having a return driver according to an embodiment of the present invention.

FIG. 4 illustrates an electroporation system 400 having a return driver 460 according to an embodiment of the present invention. Return driver may be placed before or after an array of sample plate 420, e.g., on sample plate 200. Lines indicate electrical connections and arrows indicate the flow of information, such as control signals or data.

In electroporation system 400, a control processor (CP) 430 selects from a set of capacitors 410. In one aspect, the capacitors 410 are electrolytic and do not drift significantly with time. Thus, the capacitors may be measured in manufacturing, and their values are stored in a memory 432, such as flash RAM, of the electroporator system. Accordingly, an accurate selection of capacitance may be obtained by looking up the capacitance of the available capacitors in memory 432 and selecting the combination of capacitors that best approximates the desired capacitance. In another embodiment, the capacitances may be measured by the system, for example, by charging and discharging capacitors 410 and measuring the time constant.

In one embodiment, CP 430 communicates with a graphical user interface (GUI) processor 435 to obtain parameters from an input 440, such as a keyboard, and/or memory 445, such as non-volatile RAM. Memory 445 and memory 432 may be the same memory module or different ones. Information received from GUI processor 435 can be put on the display 450. The GUI processor 435 or CP 430 can communicate to an external computer 455 for downloading or uploading data.

CP 430 directs the charging of the one or more selected capacitors 410 through the charging circuit 405. In one embodiment, charging circuit 405 overcharges capacitance 410. CP 430 then turns off charging and waits for the voltage to decrease to the desired level. CP 430 can monitor the voltage on capacitance 410 to determine when the desired voltage is achieved. Having a certain amount of time between charging and connecting the capacitor 410 to sample plate 420 decreases the noise in the electrical pulse as noise can come from, e.g., the high frequency switching regulator.

In one embodiment, interlock 418 informs CP 430 when the cable to the chamber, which holds the plate, is plugged-in, the lid is closed, a sample plate 420 is in-place, and that high voltage is present at the plate. The voltage on capacitors 410 can be compared to that provided at the plate, e.g., by a monitoring line from interlock 418. In one aspect, the interlock is a series of interlocks. One interlock opens voltage to the interlock line when the lid is opened slightly, and when the plate is not there. Also, when the power is off or the cable from the chamber to the system 400 is just slightly unplugged, electromechanical switches (relays) open because power to them is removed by detaching the cable. This eliminates electronics for that control, and meets safety/regulatory requirements.

When the voltage on the capacitors 410 reaches the desired voltage, a high voltage (HV) switch 415 is turned "on" (closed). HV switch 415 may also be a driver with programmable parameters, such as number of pulses, pulse duration, and bursts of pulses. An electrical pulse is transmitted from capacitors 410 to one or more banks of sample plate 420. CP 430 controls which banks receive the electrical pulse by sending control signals to latches 470 and return drivers 460. In one aspect, latches 470 hold drivers 460 on or off. In one aspect, latches 470 may be used to expand the number of outputs of the control processor 430. For example, multiple latches can share the same 8-bit data bus with each latch being controlled by one additional line. Hence, if one wants 16 output lines for the processor, one needs the 8-bit data bus plus two more lines for a total of ten for 16-lines. Adding eight more lines may then uses one additional processor line.

In one embodiment, the electrical pulse is transmitted through an electrical connector 422 that is connected with a common pad 424 of sample, e.g., common pad 310 from FIG. 3. Electrical connector 422 may be connected to the high voltage side or the low voltage side (e.g., ground) of the circuit. Return drivers 460 also may connect to either side of sample plate 420.

Following the sending of one electrical pulse, CP 430 can select, based on the input parameters, a new set of return drivers to be connected, and thus a new set of banks (i.e. a channel) are chosen to receive the next electrical pulse. CP 430 communicates to latches 470 which of the return drivers should be closed (on) during the next electrical pulse. One or more of the drivers 460 may be "on" at any one time during any of the electrical pulses. Drivers 460 can be selected in any order and number In one embodiment, system 400 includes a current diverter circuit that diverts current flow away from the cuvette when an arc event or low sample resistance is detected, as described in U.S. Pat. No. 6,258,592. In one aspect, HV switch 415 is turned-off at high speed when the current in the load rises sufficiently (when arc begins). Otherwise, drivers 460 could be damaged.

Depending on the number of banks chosen the sample resistance will differ. Accordingly a parallel resistance 425 may vary to provide a proper waveform for the electrical pulse. Thus, in one aspect, CP 430 provides control signals to a pulse modulated resistor (RPM) 425 to vary the parallel resistance (e.g., using techniques described in provisional patent application 60/826,422).

In one embodiment, system 400 allows up to 24 different channels, each having a different setting for waveforms, voltages, time constants, capacitors, and parallel resistance 425. In one aspect, this allows ease of gene turn-off and optimization experiments.

In one embodiment, system 400 allows the flexibility to choose how many wells receive each electrical pulse and also to input the parameters at once for all of the electrical pulses that are that are to be performed for a given sample plate. The system then automatically provides all of the electrical pulses.

Figure 5:
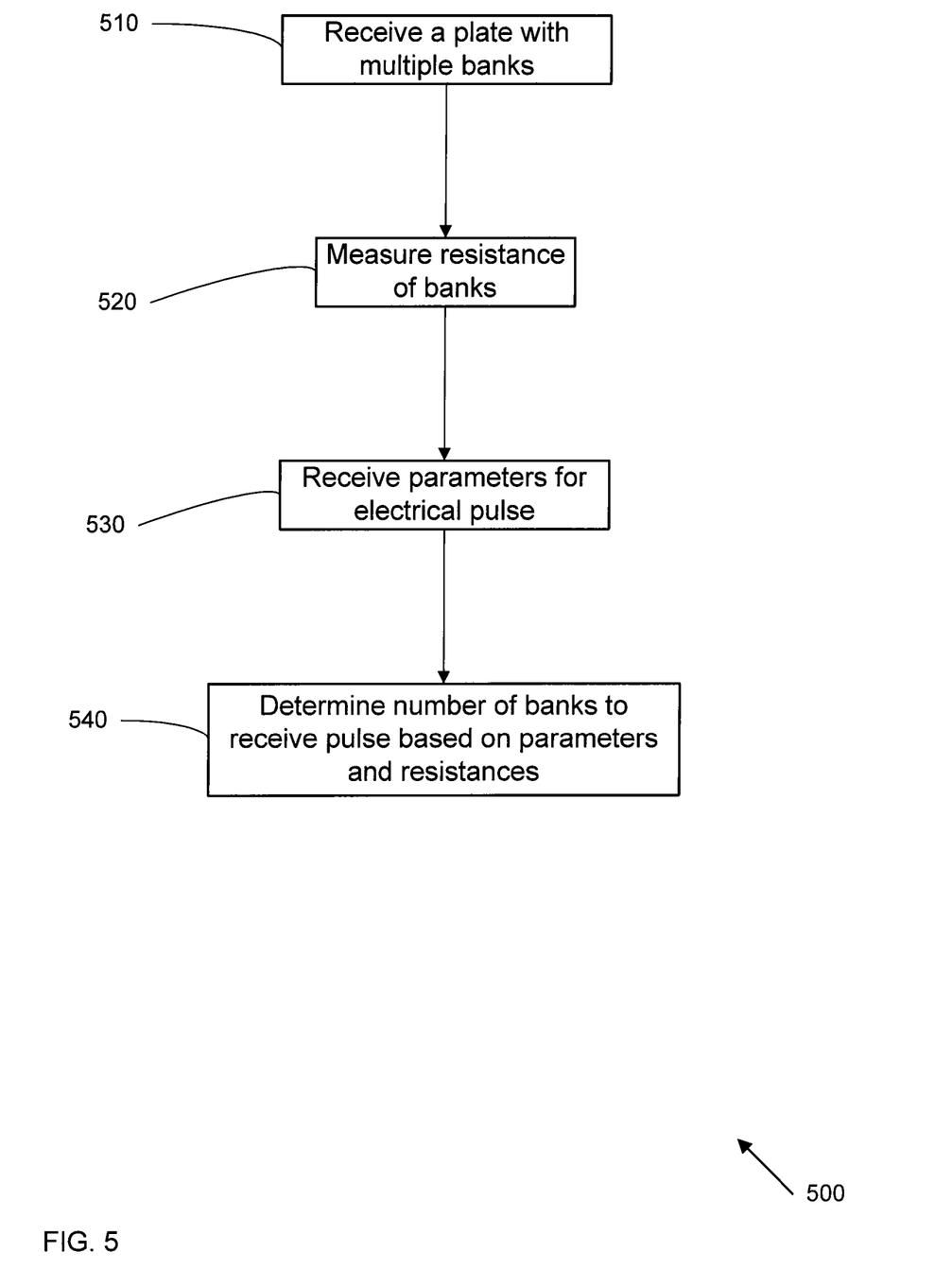
FIG. 5 illustrates a method for determining the number of banks to which to deliver an electrical pulse according to an embodiment of the present invention.

FIG. 5 illustrates a method for determining the number of banks in which to deliver an electrical pulse. In step 510, a plate with multiple banks is received. In step 520, the resistances of the banks are measured, which may be done, e.g., by any method of Ragsdale I. In one aspect, this is done to get an estimate of whether the sample load has a high resistance or low resistance, thus strict accuracy may not be required. For example, the measurement may include only determining whether or not the resistance is above or below a certain value. In step 530, parameters for the pulse are received. In step 540, the number of banks to receive pulse based on parameters and resistances is determined.

For high throughput, it is advantageous to deliver all of the electrical pulses as quickly as possible. Thus, the time between each electrical pulse should optimally be as small as possible. Typically, charging takes the most amount of time, particularly if charging a 2475 μfarads to 500 V.

One part of the time to achieve the desired voltage is the amount of time required for capacitors 410 to decrease their charge after overcharging so that the correct voltage is reached, which can be quite long. If this time is reduced, the overall charging time will be reduced. To reduce this time, in one embodiment, one or more bleed circuits, which act as discharge circuits, are included.

Figure 6:
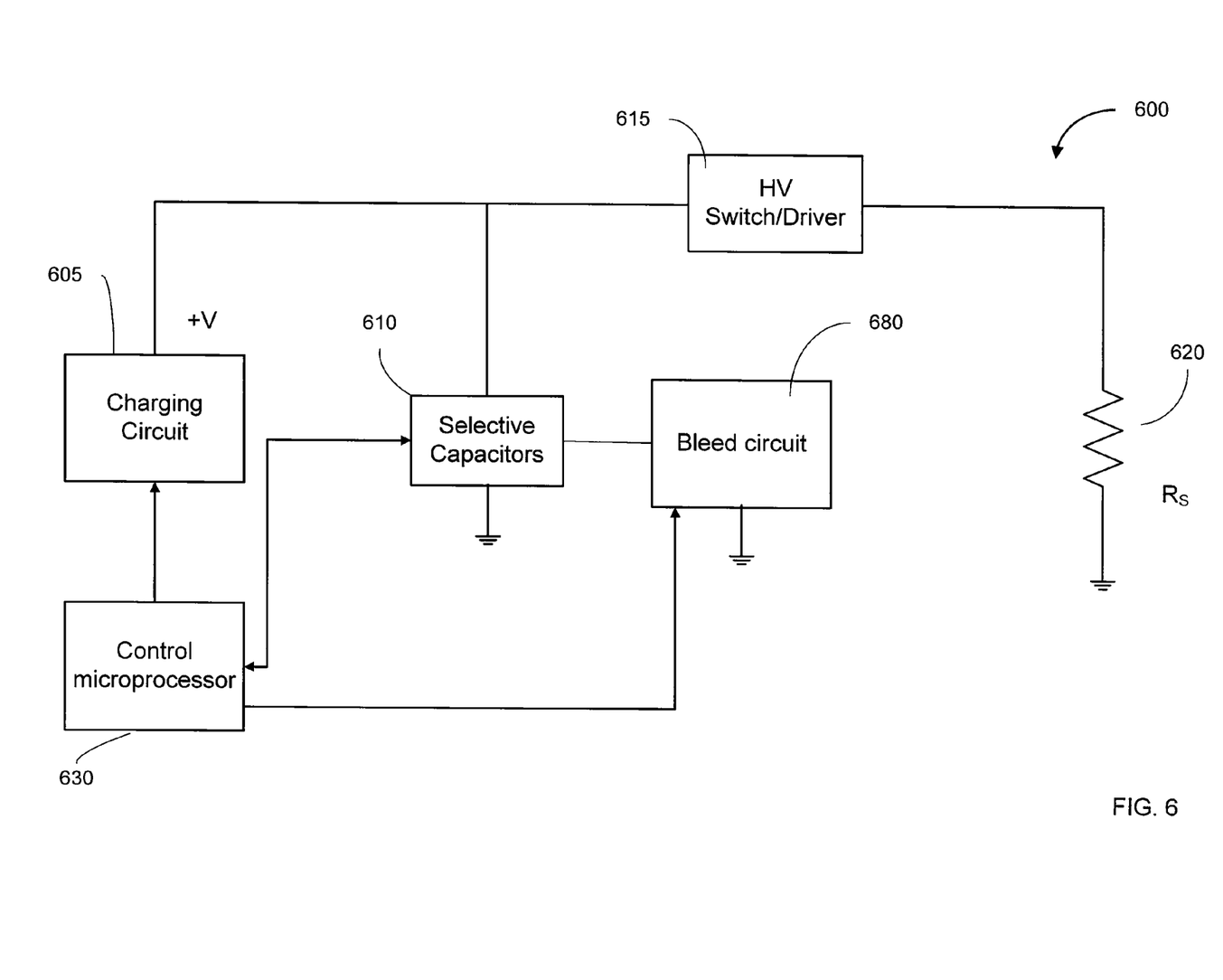
FIG. 6 illustrates an electroporation system with a bleeding circuit according to an embodiment of the present invention.

FIG. 6 illustrates an electroporation system 600 with a bleeding circuit 680 according to an embodiment of the present invention. For clarity of presentation, other components not necessary for this discussion have been left out from FIG. 6. After charging circuit 605 overcharges capacitors 610 to a higher voltage than desired, bleed circuits 680 are used to remove charge from capacitor 610 until the voltage reaches the desired level. This quicker time for charging allows all of the banks of a sample plate to be electoporated faster.

In one embodiment, a bleed circuit is a pulse modulated resistor, as described in U.S. Provisional Patent Application No. 60/826,422. Accordingly, the bleed can be controlled by changing the resistance of the bleed circuit.

Different capacitances lose charge at different rates. Thus, a large capacitance would require a different bleed circuit than a small capacitance. Otherwise, in some instances, the charge may be decreased too fast so that the desired voltage is missed, or that the decrease in charge is too slow to be of much benefit. Thus, in one embodiment, there is a different bleed circuit for different ranges of capacitance. In another embodiment, there is a different bleed circuit for different ranges of voltages. A bleed circuit may also be chosen based on a combination of capacitance and voltage values.

Accordingly, CP 630 can select the appropriate capacitors 610 and direct charging circuit 605 to overcharge the capacitance 610. CP 630 can then select, based on the capacitors selected, the appropriate bleed circuit 680 to decrease the charge. Then HV switch 615 may be turned "on," providing an electrical pulse to sample 620.

In some electroporator systems, the voltage of the capacitors is decreased to a very low level before a different set of selected capacitors are charged. This time for the voltage to drop can be significant, particularly when many electrical pulses need to be delivered to many banks of a single plate. To this end, a charge dumping circuit is provided in an electroporation system to decrease the time between two electrical pulses. For example, after a square wave or exponential with a short pulses, the charge left in the capacitor could be dumped.

Figure 7:
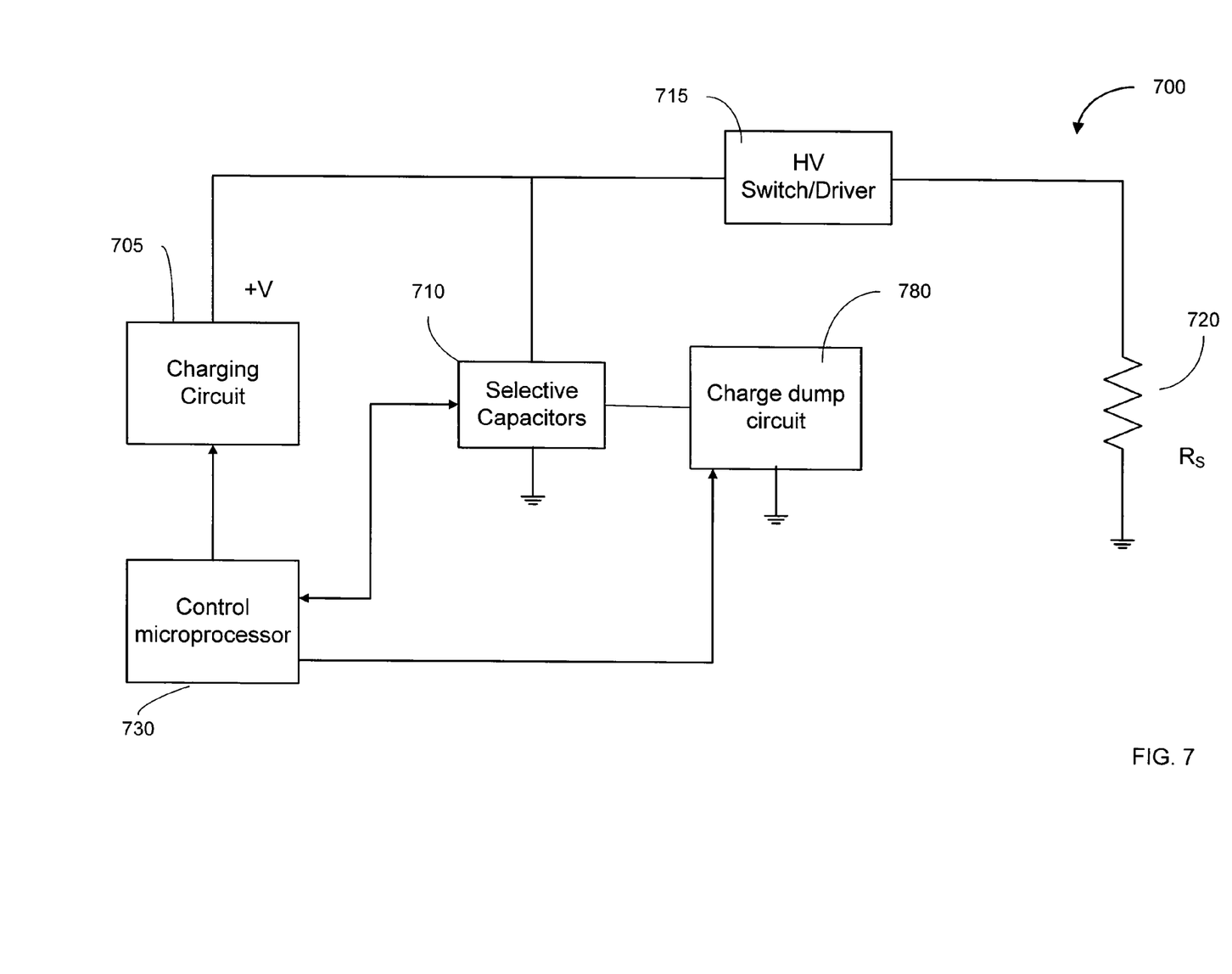
FIG. 7 illustrates an electroporation system with a charge dumping circuit according to an embodiment of the present invention.

FIG. 7 illustrates an electroporation system 700 with a charge dumping circuit 790 according to an embodiment of the present invention. Charge dumping circuit 790, which also acts as a discharge circuit, allows a very quick method for lowering the charge on capacitors 710. In one embodiment, charge dumping circuit 790 includes a switching device, such as silicon-controlled rectifier (SCR) or an insulated gate bipolar transistor (IGBT), attached to a resistance which can be triggered by the control processor.

After charging circuit 705 charges capacitors 710 and an electrical pulse has been delivered, capacitors 710 still may have a higher voltage than desired. The desired voltage may be zero (ground), near zero, or simply a lower voltage that is close to the voltage setting for the next electrical pulse. Thus, after one electrical pulse has been delivered, a charge dump circuit 790 removes the charge on capacitors 710.

In some embodiments, a smart dump may be made. In these instances, capacitors 710 do not need a low level of charge on them before they are re-charged. Also, the electrical pulse does not decrease the voltage on the capacitors 710 to zero. In a smart dump, the charge on the capacitors at the end of a pulse is utilized. In instances, where the next voltage is less than the present voltage on the capacitors, the dumping circuit only dumps enough charge to bring the voltage at or near the desired value. Then HV switch 715 may be turned "on," providing the next electrical pulse to sample 720. Note that the current voltage of the capacitors 710 is monitored by CP 730. For example, the next channel might be 50 volts after a square wave of 200 volts.

In one aspect, the dumping circuit 790 decreases the voltage to just below the correct value, and then an overcharge and bleed brings the voltage to the desired value. In one embodiment, if the desired voltage is greater than the last charge, no dump is required.

In one embodiment, the bleed circuits 680 and the charge dump circuit 790 are be the same set of circuits. In another embodiment, different circuits are used. In either instance, for different capacitances and/or voltages, different charge dump circuits may be used. Additionally, if the voltage drop to be performed is quite high, more than one charge dump circuit may be employed. For instance, one charge dump circuit may be employed to quickly reduce the voltage by a first amount; however, in order to not move past the desired voltage, a second charge dump circuit could be employed for reducing the voltage the last amount to achieve the desired voltage. In another embodiment, the resistance of a pulse modulated resistor can be changed to control the reduction in the voltage.

While the invention has been described by way of example and in terms of the specific embodiments, it is to be understood that the invention is not limited to the disclosed embodiments. To the contrary, it is intended to cover various modifications and alternatives, in addition to those described above, as would be apparent to those skilled in the art. Therefore, the scope of the appended claims should be understood as encompassing all such modifications and alternatives.

What is claimed is:

1. An electroporation system capable of providing an electrical pulse to one or more samples, the electroporation system comprising:

a capacitance;

a charging circuit configured to charge the capacitance;

a first electrical connector adapted to connect with a common pad of a sample plate having a plurality of banks, each having a plurality of wells, wherein when the first electrical connector is connected with the common pad, the first electrical connector is connected with a first electrode of each well of the banks;

a plurality of drivers, each adapted to connect with one of a plurality of separate pads of the sample plate, wherein when a driver is connected with a separate pad, that driver is connected with a second electrode of each well of one bank, wherein a state of that driver determines whether an electrical pulse is transmitted from the capacitance to the one bank connected with that driver; and a control processor configured to:

prior to transmitting the electrical pulse from the capacitance to a bank, determine a resistance of a sample in the wells of the banks;

based on the determined resistance, select one or more banks for delivering an electrical pulse from the capacitance; and control the state of the drivers such that the electrical pulse is transmitted to the selected banks, wherein prior to the selection of the one or more banks to send the electrical pulse, the control processor is configured to determine a number of banks to be selected based on:

an operating range of one or more circuit components of the electroporation system that are used to provide the electrical pulse to the selected banks; and the determined resistance,
wherein the number of banks is variable, and wherein the possible values for the variable number of banks include one bank and a plurality of banks.

2. The system of claim 1, wherein the control processor is further configured to determine, based on the determined resistance, a maximum number of banks to which the system is capable of delivering the pulse.

3. The system of claim 1, wherein the drivers are operable such that an electrical pulse is transmitted to all of the banks.

4. The system of claim 1, wherein the drivers are connected with the capacitance and the first electrical connector is connected with ground.

5. The system of claim 1, wherein the drivers are connected with ground and the first electrical connector is connected with the capacitance.

6. The system of claim 1, further comprising:
a memory element configured to store parameters for each electrical pulse to be delivered to the banks of the sample plate, wherein the parameters include which banks to deliver each electrical pulse.

7. The system of claim 1, further comprising:
a control processor that independently controls the state of each of the drivers.

8. A method of using an electroporation system to deliver an electrical pulse to a sample plate having a plurality of banks, the method comprising:
prior to transmitting the electrical pulse from a capacitance to a bank, determining a resistance of a sample in the wells of the banks;
a control processor of the electroporation system determining a number of banks to be selected based on an operating range of one or more circuit components of the electroporation system and based on the measured resistance, wherein the number of banks is variable, and wherein the possible values for the variable number of banks include one bank and a plurality of banks;
selecting, with a control processor, one or more banks equal to the determined number of banks for delivering an electrical pulse from a capacitance;
charging a capacitance with a charging circuit;
connecting a first electrical connector with a common pad of a sample plate having a plurality of banks, each having a plurality of wells, wherein when the first electrical connector is connected with the common pad, the first electrical connector is connected with a first electrode of each well of the banks;
connecting one or more of a plurality of drivers with respective separate pads of the selected banks of the sample plate, wherein when a driver is connected with a separate pad, that driver is connected with a second electrode of each well of one bank, wherein the control processor is coupled with the charging circuit and the plurality of drivers; and
subsequent to determining the resistance of the sample in the wells of the banks and selecting the one or more banks, transmitting one or more electrical pulses from the capacitance to one or more selected banks based upon the state of the drivers.

9. The method of claim 8 wherein the control processor is coupled with the charging circuit and the plurality of drivers.

10. The method of claim 8, further comprising:
determining, based on the determined resistance, a maximum number of banks to which a system is capable of delivering the electrical pulse; and
delivering the electrical pulse to no more than the maximum number of banks.

11. The method of claim 8, wherein an electrical pulse is transmitted to all of the banks.

12. The method of claim 8, wherein the drivers are connected with the capacitance and the first electrical connector is connected with ground.

13. The method of claim 8, wherein the drivers are connected with ground and the first electrical connector is connected with the capacitance.

14. The method of claim 8, further comprising:
accessing a memory to obtain parameters for each electrical pulse to be delivered to the banks of the sample plate, wherein the parameters include which banks to deliver each electrical pulse.

15. The method of claim 14, wherein transmitting an electrical pulse from the capacitance to one or more selected banks includes:
transmitting one or more electrical pulses to only a portion of the banks, wherein the portion includes at least two of the banks.

16. The method of claim 15, wherein transmitting an electrical pulse from the capacitance to one or more selected banks further includes:
transmitting different electrical pulses to each of the selected banks.

17. The method of claim 8, further comprising:
controlling the state of each of the drivers with a control processor.

18. A method of using an electroporation system to deliver an electrical pulse to a sample plate having a plurality of banks, the method comprising:
prior to transmitting the electrical pulse from a capacitance to a bank, measuring a resistance of at least one bank;
based on the resistance and on an operating range of one or more circuit components of the electroporation system, a control processor of the electroporation system selecting one or more banks in which to deliver an electrical pulse, wherein the number of banks is variable, and wherein the possible values for the variable number of banks include one bank and a plurality of banks; and
transmitting an electrical pulse to the selected banks.

19. The method of claim 18 wherein measuring the resistance comprises determining whether the resistance is within two or more ranges of resistance values.

20. The method of claim 18 wherein measuring the resistance of at least one bank comprises measuring a resistance of each selected bank.

21. The method of claim 18 wherein measuring the resistance of at least one bank comprises measuring a resistance of each bank.

22. The method of claim 18, further comprising determining a resistance of the selected banks.

23. The method of claim 12, further comprising:
determining, based on the resistance of the selected banks, a resistance of a variable resistance device that is connected in parallel with the selected banks.

24. The method of claim 18, further comprising turning "on" a driver coupled with each selected bank.

25. The method of claim 18, further comprising
receiving one or more parameters for the electrical pulse, wherein selecting the one or more banks is also based on the parameters.

* * * * *